United States Patent [19]
Seto et al.

[11] Patent Number: 6,157,914
[45] Date of Patent: *Dec. 5, 2000

[54] MEDICAL SUPPORT SYSTEM

[75] Inventors: Hiromitsu Seto; Eitaro Nishihara, both of Ootawara; Yuki Fukushima, Tochigi, all of Japan; Mohammad Ali Nematbakhsh, Anaheim, Calif.

[73] Assignee: Kabushiki Kaisha Toshiba, Kawasaki, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/714,521

[22] Filed: Sep. 16, 1996

Related U.S. Application Data

[63] Continuation of application No. 08/019,866, Feb. 19, 1993, abandoned.

[30] Foreign Application Priority Data

Feb. 21, 1992 [JP] Japan ................................. 4-035329

[51] Int. Cl.⁷ .................................................. G06F 159/00
[52] U.S. Cl. ................................................................ 705/3
[58] Field of Search ..................................... 395/201–203, 395/601; 360/825.49, 825–52; 705/1–3; 707/1, 100, 200, 10, 201, 204; 283/54; 340/286.07, 286.08

[56] References Cited

U.S. PATENT DOCUMENTS

| | | | |
|---|---|---|---|
| 4,007,355 | 2/1977 | Moreno | 235/61.7 |
| 4,491,725 | 1/1985 | Pritchard | 235/375 |
| 4,632,428 | 12/1986 | Brown | 283/76 |
| 4,817,050 | 3/1989 | Komatsu et al. | 364/900 |
| 4,847,694 | 7/1989 | Nishihara | 358/434 |
| 4,897,865 | 1/1990 | Canuel | 379/144 |
| 4,958,283 | 9/1990 | Tawara et al. | 364/413.13 |
| 5,099,424 | 3/1992 | Schneiderman | 364/413.02 |
| 5,140,518 | 8/1992 | Ema | 364/413.01 |
| 5,235,510 | 8/1993 | Yamada et al. | 364/413.02 |
| 5,469,353 | 11/1995 | Pinsky et al. | 705/3 |
| 5,530,232 | 6/1996 | Taylor | 235/380 |

FOREIGN PATENT DOCUMENTS

| | | |
|---|---|---|
| 62-181005 | 8/1987 | Japan . |
| 4-21196 | 1/1992 | Japan . |

OTHER PUBLICATIONS

Lindgerg, "Statewide Medical Information System", dialog file 6, Accession No. 0543972, Apr. 1970.

Eich, "HoneyWell Introduces Computer Network Facility for Hospitals", Chicago, IL, Jul. 29, 1985, Dialog file 621, Accession No. 00102603.

Govoni, Focussing care on new technology (health care), InformationWeek No.358 p.22–3, Feb. 3, 1992, Dialog file 2, Accession No. 04114463.

(List continued on next page.)

*Primary Examiner*—Frantzy Poinvil
*Attorney, Agent, or Firm*—Oblon, Spivak, McClelland, Maier & Neustadt, P.C.

[57] ABSTRACT

A medical support system intended to centrally manage medical information generated by more than one hospital and permit medical information interchange among hospitals with easy operations. The system includes a plurality of storage units for storing medical information about patients, an entry unit for entering identification information for identifying a specific patient, an identifying unit for identifying storage units that store medical information about the specific patient on the basis of the identification information from the entry unit, and an access unit for accessing the storage units identified by the identifying unit by storage units identification information to read the medical information about the specific patient.

15 Claims, 12 Drawing Sheets

OTHER PUBLICATIONS

"In Search of the Right Card for Swiss Medical System", Videoprint Dec. 9, 1985 p.81, Dialog file 16, Accession No. 01287442.

Everest, Database Management, Objectives, Functions and Administration, McGraw–Hill Book Company, 1986 pp. 732–781.

Optoelectronic Industry and Technology Development Association, "Development Report of Optical Technology—Applied Project—Medical Information System Based on Applied Optics," Mar. 1998, pp. 3–4.

Tachisawa, "Medical Application of IC Card and Optical Card, And Future Prospects," Aimikku (Transliterated), 1986, vol. 7, No. 3, pp. 4–11.

| HOSPITAL | HOSPITAL ID |
|---|---|
| HOSPITAL A | 000001 |
| HOSPITAL B | 000002 |
| HOSPITAL C | 000003 |
| HOSPITAL D | 000004 |
| HOSPITAL E | 000005 |
| HOSPITAL F | 000006 |
| HOSPITAL G | 000007 |

FIG. 5

| CITIES, TOWNS, VILLAGES |
|---|
| AAAAA CITY |
| BBBBB CITY |
| CCCCC TOWN |
| DDDDD TOWN |
| EEEEE TOWN |
| FFFFF VILLAGE |

FIG. 6

| OTHER AREA | SYSTEM ID |
|---|---|
| GGGGGG CITY | 00000001 |
| HHHHHH CITY | 00001034 |
| IIIIII TOWN | 00000021 |
| JJJJJJ TOWN | 01459671 |
| KKKKKK CITY | 00789321 |
| LLLLLL VILLAGE | 00032957 |
| MMMMMM TOWN | 02569012 |
| NNNNNN CITY | 00235697 |
| OOOOOO TOWN | 09034256 |

FIG. 7

```
         ┌─────┐  ┌──────────────┐
         │ END │  │ CONTINUATION │
         └─────┘  └──────────────┘
NAME :
ADDRESS :
NEW / OLD :

ID :

DATE OF          :
FIRST TREATMENT

DATE OF          :
LAST TREATMENT

DEPARTMENT :

DOCTOR :
```

F I G. 8

| | | |
|---|---|---|
| | IDENTIFICATION INFORMATION | B—AAAAA CITY |
| | HOSPITAL ID | 000002 |
| | CASE ID | 000359 |
| SIMPLIFIED HISTORY DATA | DATE OF FIRST TREATMENT | 1991. 03. 07 |
| | DATE OF LAST TREATMENT | 1991. 05. 30 |
| | DEPARTMENT | SURGERY |

F I G. 9

| CASE IDENTIFICATION INFORMATION | HOSPITAL ID | CASE ID | DATE OF FIRST TREATMENT | DATE OF LAST TREATMENT | DEPARTMENT |
|---|---|---|---|---|---|
| A-BBBBB CITY | 000001 | 134568 | 1984.10.01 | 1984.10.15 | INTERNAL MEDICIHE |
| A-BBBBB CITY | 000001 | 134568 | 1990.03.16 | 1990.03.19 | SURGERY |
| A-BBBBB CITY | 000001 | 134568 | 1991.03.01 | | INTERNAL MEDICIHE |
| B-AAAAA CITY | 000002 | 000359 | 1973.08.23 | 1973.08.10 | INTERNAL MEDICIHE |
| D-CCCCC TOWN | 000003 | 010025 | 1990.07.05 | 1990.07.25 | SURGERY |
| E-CCCCC TOWN | 000002 | 001032 | 1991.03.07 | | PEDIATRICS |
| F-AAAAA CITY | 000003 | 050157 | 1991.02.12 | | INTERNAL MEDICIHE |

|  | END | CONTINUATION |
|---|---|---|
| NAME : | | |
| ADDRESS : | | |
| CASE ID : | | |

FIG. 12

| CASE IDENTIFICATION INFORMATION | HOSPITAL ID | CASE ID | DATE OF FIRST TREATMENT | DATE OF LAST TREATMENT | DEPARTMENT |
|---|---|---|---|---|---|
| E-CCCCC | 000003 | 010025 | 1990.07.05 | 1990.07.25 | SURGERY |
| E-CCCCC | 000002 | 010025 | 1991.03.07 | | PEDIATRICS |

MEDICAL SUPPORT SYSTEM

This application is a continuation of application Ser. No. 08/019,866, filed on Feb. 19, 1993, now abandoned.

BACKGROUND OF THE INVENTION

1. Field of the Invention

The present invention relates to a medical support system which centrally manages medical information such as medical charts and medical images such as X-ray images created by more than one hospital.

2. Description of the Related Art

A hospital has a wide variety of jobs such as dealing with arriving people, examining patients, hospitalizing patients, producing X-ray photographs of patients and so on. Thus, various pieces of information, such as medical charts, X-ray photographs, etc., (hereinafter referred to as medical information) are produced. Considerable labor is required to manage such medical information.

In order to meet the problem, a medical information storage system has been developed that uses a database technique. This medical information storage system is constructed by connecting terminals at various locations, such as a reception office, consulting rooms, X-ray inspection rooms, etc., to a database by use of data lines. The system aims to implement a series of jobs ranging from creation of information to acquisition and storage of it with easy operations.

In most cases medical information about a patient is utilized within one and the same hospital. However, in the case where past examination results for a new patient have been stored in another hospital, any hospital may need them.

In such a case, at present, a request is made to that hospital for a copy of the past examination results. However, it takes too long from when a request is made until a copy of the past examination results is obtained. In case of emergency, therefore, it is impossible to check the past examination results. Further, in most cases it is a patient himself or herself that fetches a copy of past examination results from a hospital where he or she had a medical examination previously. This may present a problem concerning security protection of medical information.

It is therefore desired to build a wide area system which links medical information storage systems of hospitals by telephone lines so as to enable medical information to be interchanged among hospitals. However, many difficulties are encountered in building such a wide area system because each hospital has installed a medical information storage system individually and thus the data structure and the information retrieval procedure may differ among hospitals.

SUMMARY OF THE INVENTION

It is an object of the present invention to provide a medical support system which centrally manages medical information created by more than one hospital and permits medical information to interchange among hospitals with easy operations.

According to the present invention there is provided a medical support system comprising:

- a plurality of storage means each storing medical information about patients;
- entry means for entering identification information for identifying a specific patient;
- identifying means responsive to the identification information for identifying one of the plurality of storage means that stores medical information about the specific patient; and
- access means for accessing the storage means identified by the identifying means by the identification information to read out medical information about the specific patient.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

DETAILED DESCRIPTION OF THE PREFERRED EMBODIMENTS

Figure 1:
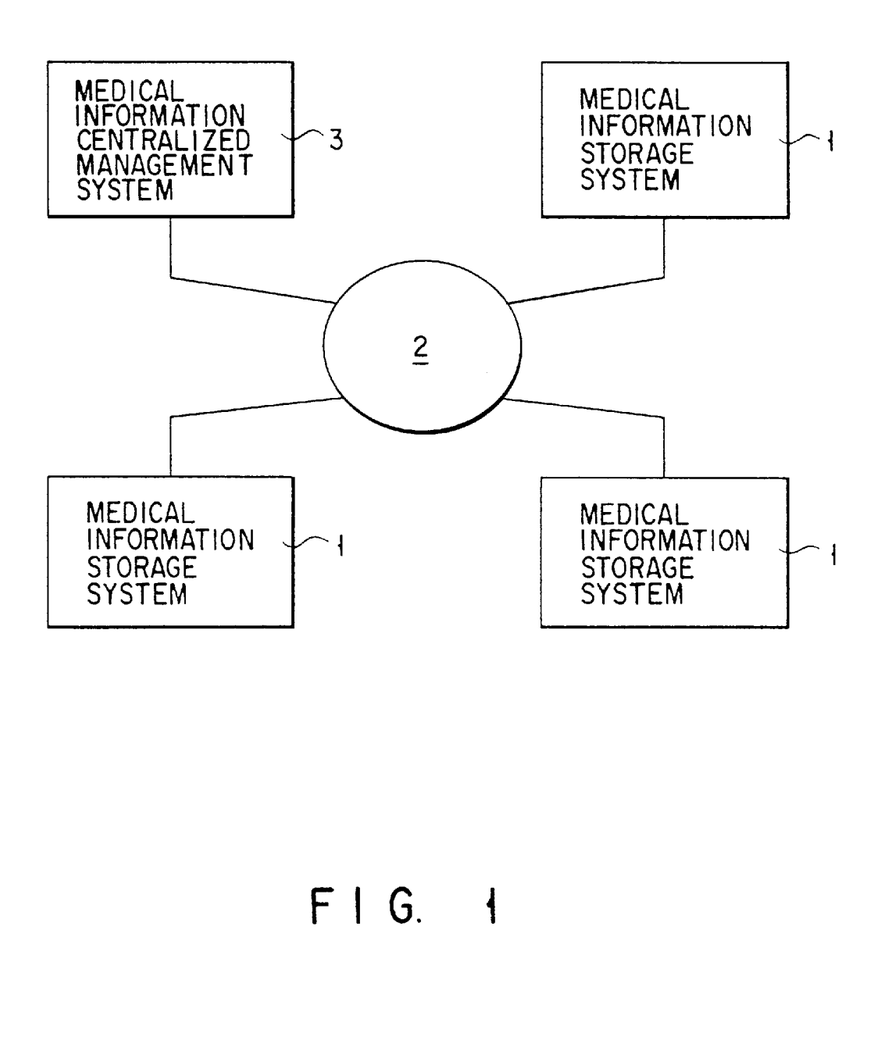
FIG. 1 is a block diagram of the entire configuration of a medical support system according to an embodiment of the present invention.

Referring now to FIG. 1, there is shown a medical support system according to a first embodiment of the present invention. In this system, each of medical information storage systems 1, which have been installed in hospitals, stores various types of medical information such as medical charts and diagnostic images. The medical information storage systems 1 are interconnected by a communication network 2 such as telephone lines. Each of the systems 1 is located in an administrative unit area (hereinafter referred to as unit area for the convenience of description) such as an area to which an ambulance or ambulances are assigned. A medical information centralized management system 3 is connected to the communication network 2 so as to centrally manage the medical information storage systems 1 for the unit areas. The medical information centralized management system 3 is installed in a central hospital within the unit areas.

Figure 2:
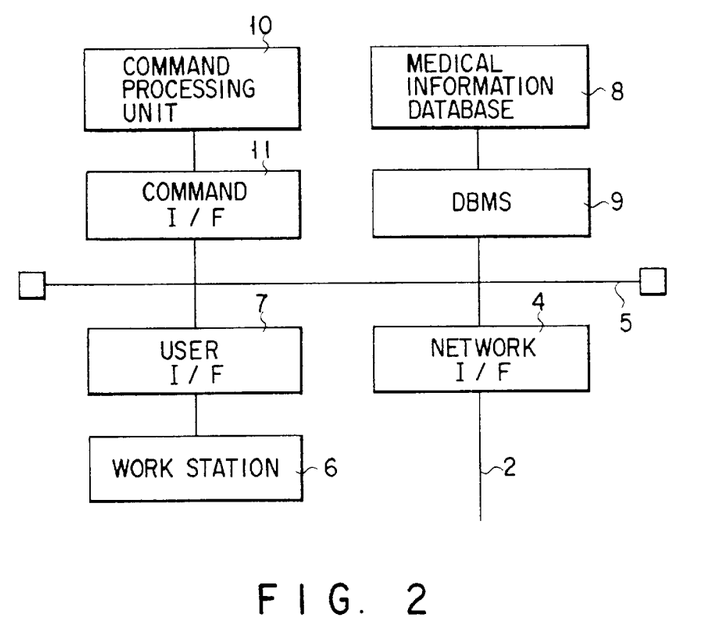
FIG. 2 is a block diagram of the medical information storage system of FIG. 1.

The medical information storage system 1 is configured as shown in FIG. 2. A bus 5 is connected to the communication network 2 by an network interface (I/F) 4. A work station 6 is connected to the bus 5 by a user I/F 7. A number of work stations 6, which are terminals installed in various locations in a hospital such as a reception office and various departments for diagnosis and treatment, are used to perform various processes of, for example, entering bibliographic items such as names of patients, their addresses, their dates of attendance at the hospital, and their identifiers (patient ID's, e.g., insurance numbers). These bibliographical items are stored in a medical information database 8 together with images generated by various modalities not shown, such as a computerized tomography apparatus and an X-ray diagnostic apparatus, which are connected to the bus 5. A database management system (DBMS) 9, which is a management unit for the medical information database 8, has directory information derived from medical information. A command processing unit 10 is connected to the bus 5 by a command I/F 11 to execute various processes according to various commands from the work station 6, in this example, four commands of entry, update, retrieval, and emergency. Upon receipt of an entry command, the command processing unit 10 transfers bibliographical items input from the work station 6 as well as that command to the medical information centralized management system 3. The processes for other commands will be described later.

Figure 3:
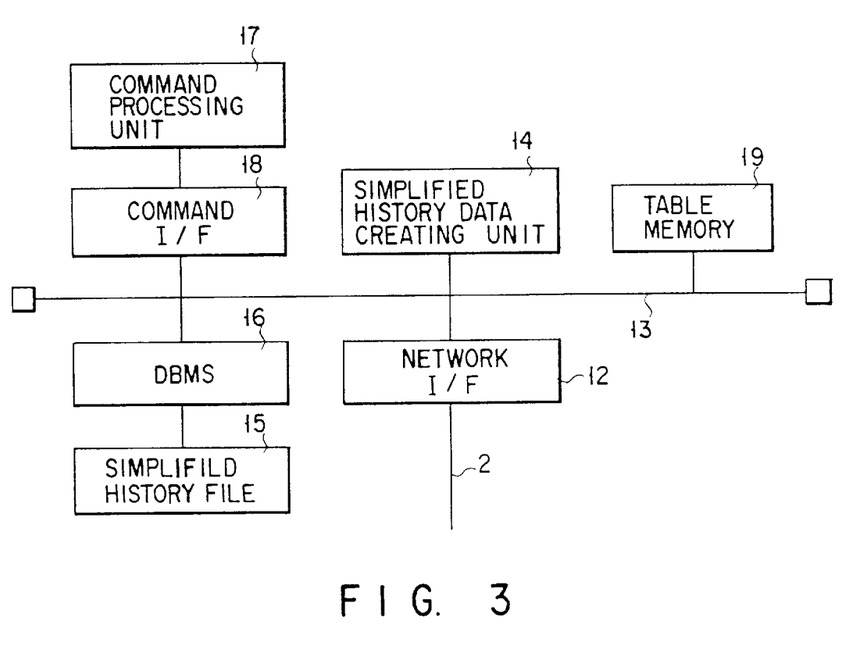
FIG. 3 is a block diagram of the medical information centralized management system of FIG. 1.

The medical information centralized management system 3 is configured as shown in FIG. 3. A bus 13 is connected to the communication network 2 by a network I/F 12. To the bus is connected a simplified hospital-attendance history data creating unit 14 which extracts from the bibliographical items sent from the medical information storage system 1 predetermined fundamental items which any hospital needs and appends an identifier of a hospital (hospital ID) which sent the bibliographical items to the extracted items to create index data (hereinafter referred to as simplified history data for the convenience of description). The simplified history data is sent to a simplified history file database 15 to create a simplified history file. Thus, all information generated in the above unit areas is integrated in a simplified format in the simplified history file. A database management system 16, which is a management unit for the simplified history file database 15, has directory information derived from the simplified history data. A command processing unit 17 receives commands sent from the medical information storage system 1 via a command I/F 18 to perform various processes. These processes will be described later.

Figure 4:
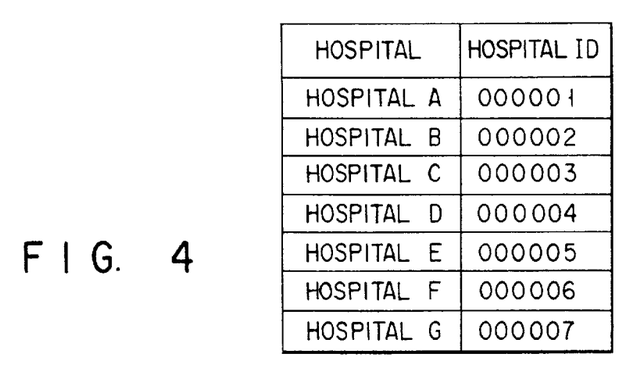
FIG. 4 is a hospital identification (ID) table.
Figure 5:
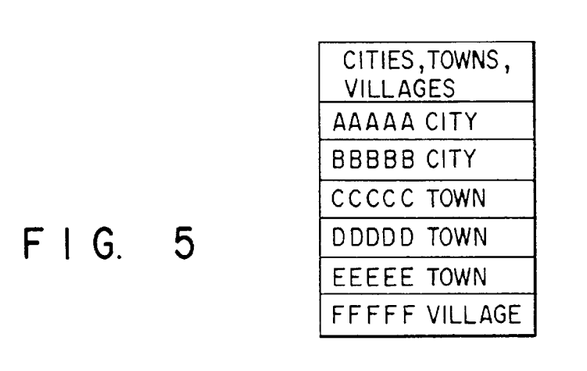
FIG. 5 is a table listing cities, towns, and villages.
Figure 6:
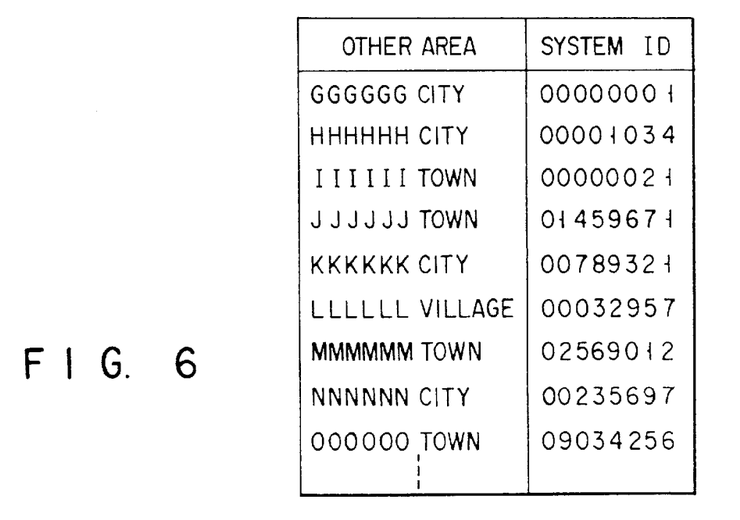
FIG. 6 is a table of medical information centralized management system ID's in other areas.

A table memory 19 is connected to the bus 14. The table memory stores a hospital ID table which makes hospitals within the unit areas correspond one for one with identifiers as shown in FIG. 4, a table listing cities, towns, and villages located within the unit areas as shown in FIG. 5, and a system ID table which makes medical information centralized management systems existing within other areas than the above unit areas correspond one for one with identifiers as shown in FIG. 6.

The operation of the present embodiment will be described hereinafter.

The above commands comprise four commands of entry, update, retrieval, and emergency. The system has four modes of operation corresponding to these commands.

Figure 7:
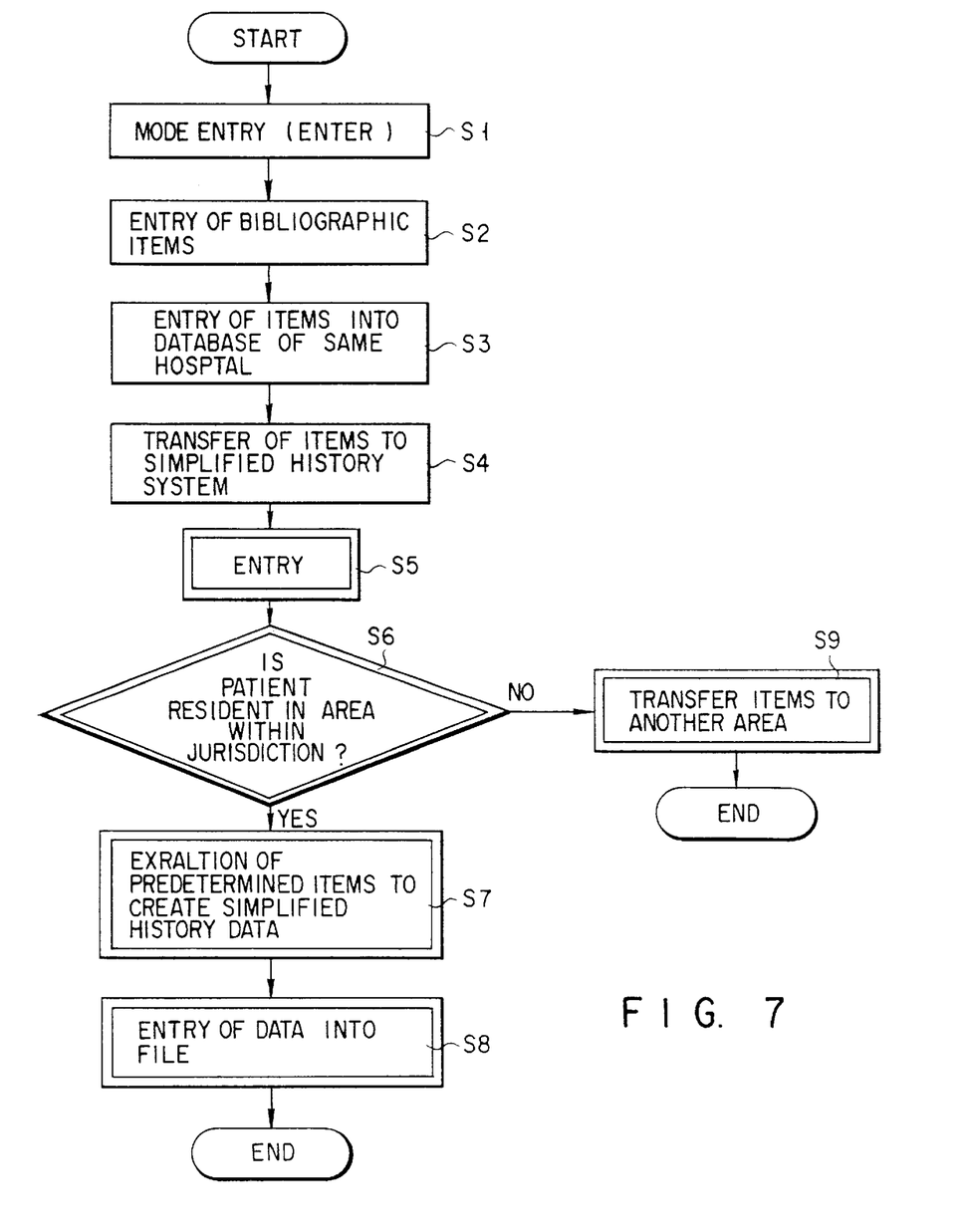
FIG. 7 is a flowchart of enter mode.

First, the flow of the entry mode will be described with reference to FIG. 7. In this figure, single-line blocks represent processing by the medical information storage system 1, while double-line blocks represent processing by the medical information centralized management system 3.

Figure 8:
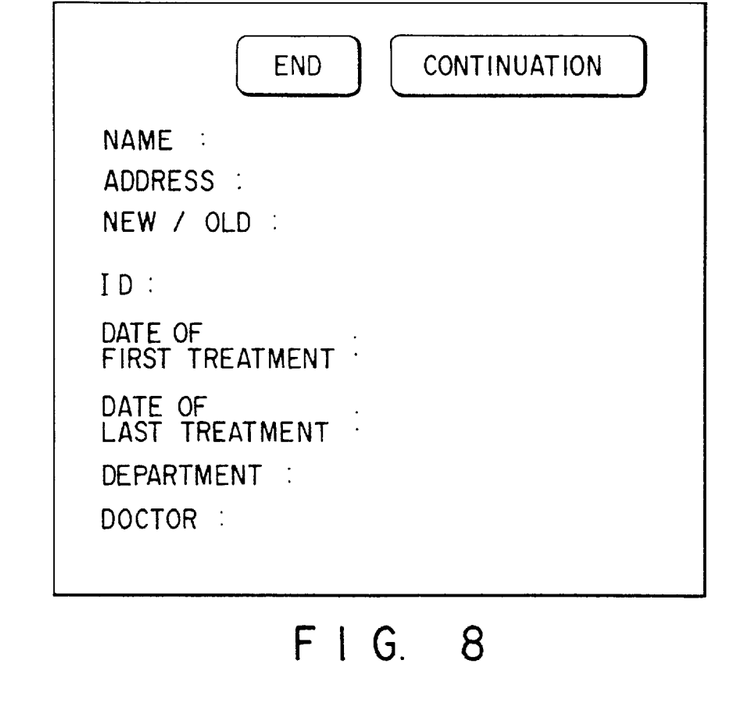
FIG. 8 shows an example of a data entry screen in the enter mode.

The entry mode is set by an operator at the work station 6 installed in the reception office when a patient comes to the hospital (S1). The command processing unit 10 is responsive to an entry command from the work station to display such an entry screen as shown in FIG. 8 on the monitor of the work station 6. This entry screen is identical to that used by the conventional medical information storage system. Bibliographical items, such as patient name, patient address, distinction between new and old cases, patient ID number such as insurance number, first consultation date, treatment department, etc., are entered according to the entry screen (step S2). Note that the date of the last treatment and a doctor in charge, which are not known at the time of the first attendance at the hospital, are added as soon as they are made known. The continuation icon is appointed when some other bibliographical item of the patient needs to be input in succession.

The termination icon is appointed upon termination of the entry of these bibliographical items, and they are transferred to and stored in the medical information database 8 in the hospital. The procedure of S1 to S3 is the same as the conventional one. Of course, depending on hospitals, there may be other procedures. Even in this case, the procedure of S1 to S3 is involved frequently.

At the termination of step S3 the command processing unit 10 transfers the entry command and the bibliographical items to the medical information centralized management system 3 (S4).

The medical information centralized management system 10 receives the entry command and the bibliographical items (S5). The command processing unit 17 decodes the entry command and starts the entry mode. First, the command processing unit 17 makes a decision as to whether the patient resides in an area within the jurisdiction of the medical information centralized management system 3 (S6). This decision is made by the use of the table of cities, towns and villages stored in the table memory 19. If YES in step S6, the bibliographical items are sent to the simplified history data creating unit 14.

Figure 9:
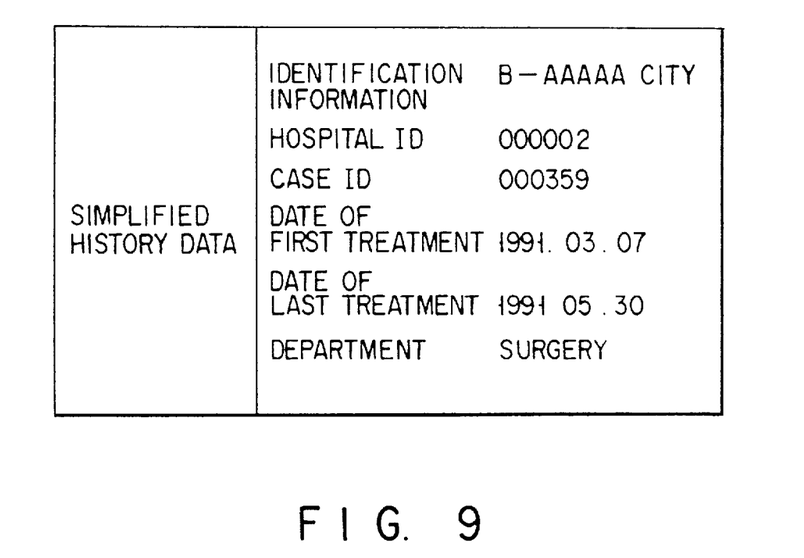
FIG. 9 shows simplified hospital-attendance history data.

The simplified history data creating unit 14 extracts from the bibliographical items the fundamental items, i.e., the patient name, the patient address, the date of the first treatment, the date of the last treatment, and the treatment department and adds the ID of the sending hospital in the hospital ID table to the fundamental items extracted, thereby creating the simplified history data shown in FIG. 9 (S7).

The simplified history data is sent to the database 19 where it is entered into the simplified history file (S8). Thus the entry mode terminates.

If NO in step S6, on the other hand, the command processing unit 17 transfers the bibliographical items to the medical information centralized management system in the other area where the patient resides (S9). In the case where that other area is provided with no medical information centralized management system, or in the case where, even if there is a medical information centralized management system, it is not connected to the communication network 2, the entry mode is terminated immediately.

Next, the update command is entered via the work station 6 when changes are made to the bibliographical items, a doctor in charge is determined, or treatment is terminated. Responsive to the update command, the command processing unit 10 causes the same entry screen as that shown in FIG. 8 to appear on the monitor of the work station. And proper data for retrieval such as patient name is input.

The data for retrieval is transferred to the medical information centralized management system 3 together with the update command. The command processing unit 17 in the medical information centralized management system 3 uses the data for retrieval to make access to the simplified history file and then transfers the simplified history data of the patient retrieved from the file to the medical information storage system 1. The simplified history data is displayed on the monitor of the work station 6. Additions and changes are entered to correct the simplified history data. This simplified history data is retransmitted to the medical information centralized management system 3 to update the simplified history file.

Figure 11A:
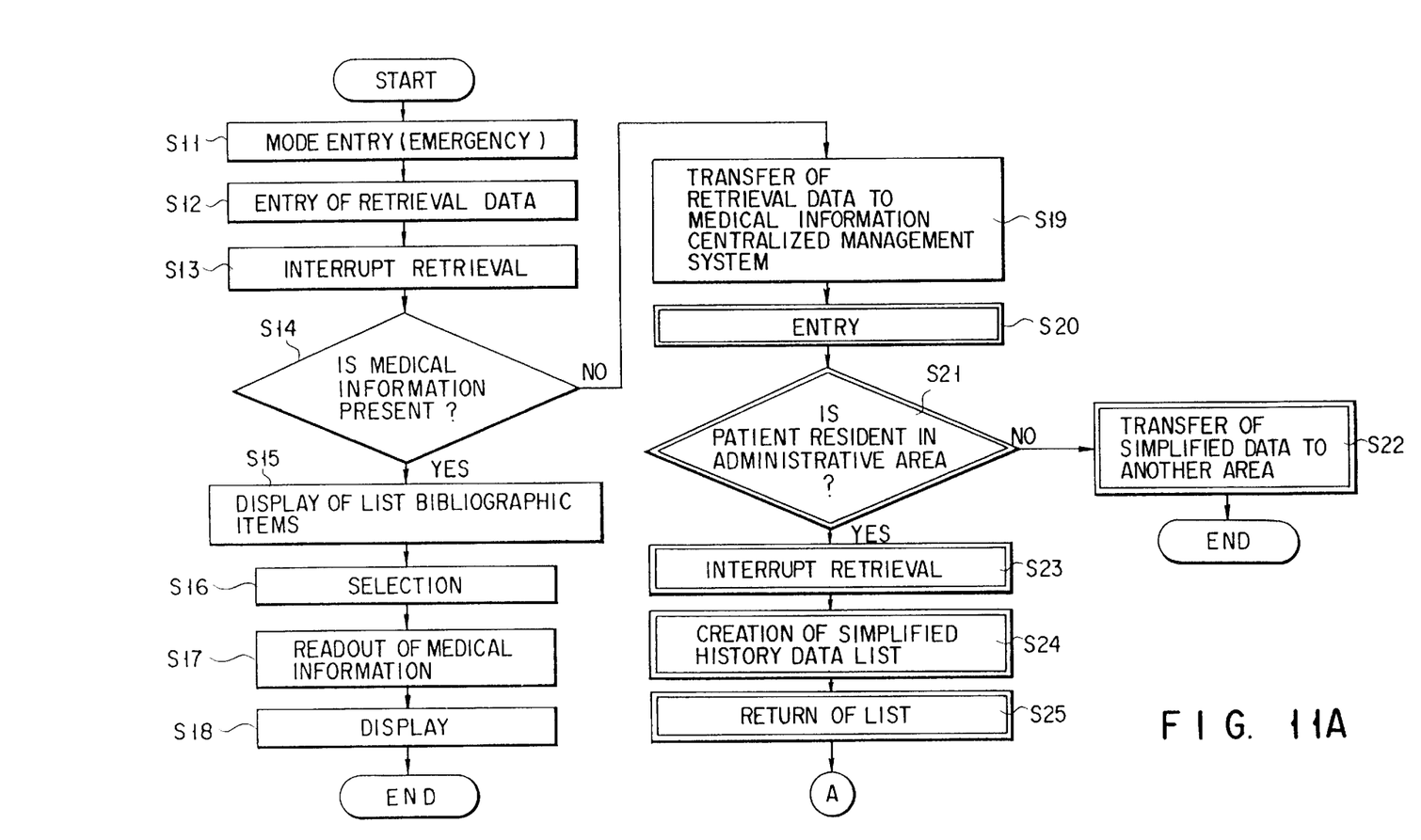
FIGS. 11A and 11B are a flowchart of emergency mode.
Figure 11B:
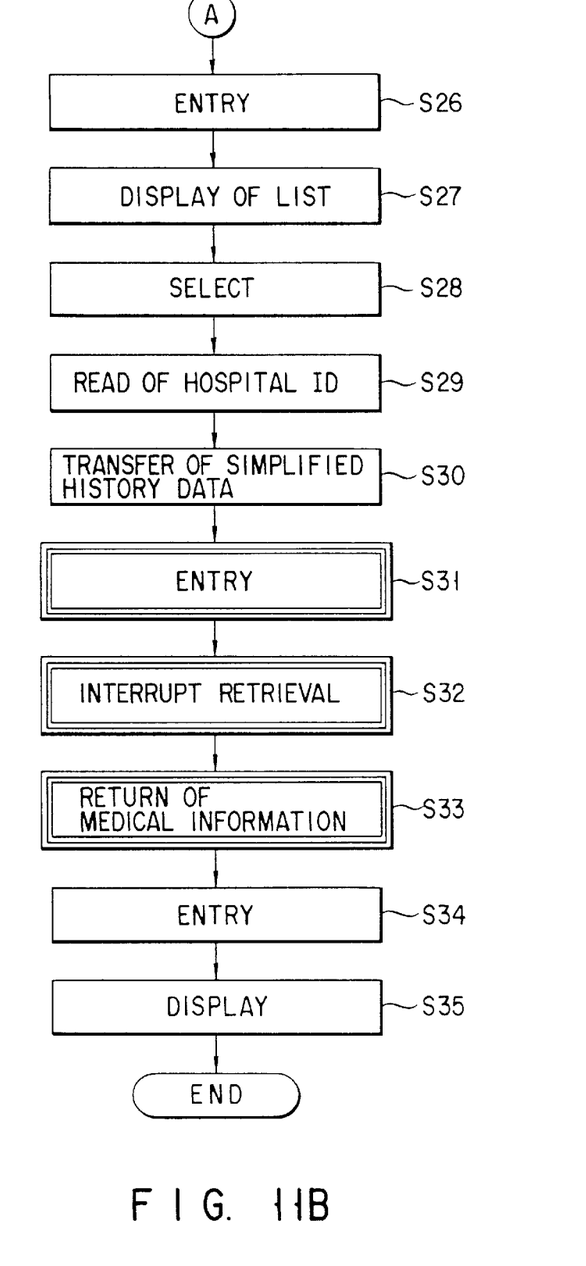

Next, reference will be made to FIGS. 11A and 11B to describe the procedure in the emergency mode. In these figures, single-line blocks represent processing by a medical information storage system 1 from which a request for retrieval was originated, double-line blocks represent processing the medical information centralized management system 3, and triple-line blocks represent processing a medical information storage system 1 which stores necessary medical information. Since the procedure in the retrieval mode is substantially the same as that in the emergency mode, the description of the procedure in the retrieval mode is omitted. However, the differences between the procedures in the retrieval and emergency modes will be described on occasion in the following description of the procedure in the emergency mode.

The emergency mode is specified when past medical information has to be viewed as soon as possible, for example, when a sudden traffic accident happened or an emergency case occurred.

Figure 12:
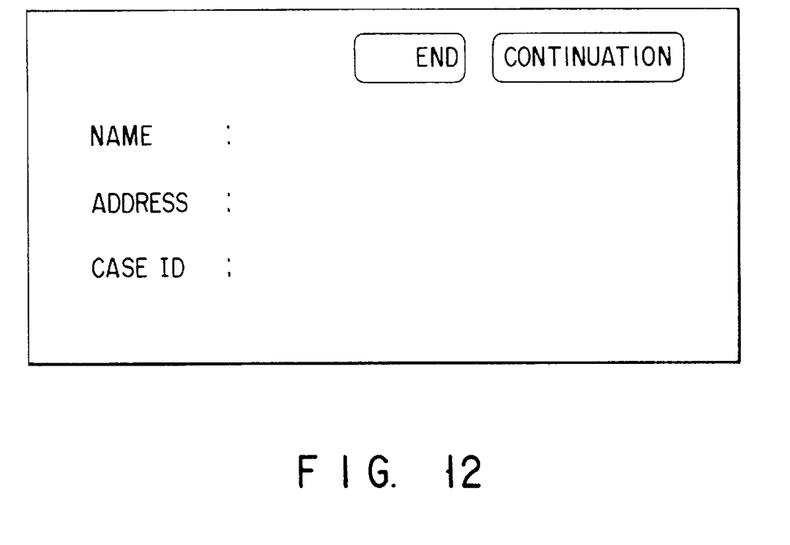
FIG. 12 shows a retrieval data entry screen.

In case of the occurrence of an emergency case, a receiving hospital is informed of the name and address of the emergency case from an ambulance. In the receiving hospital, an emergency command is entered into the medical information storage system 1 via the work station 6 (S11). Upon receipt of the emergency command, the command processing unit 10 starts the emergency mode. First, the entry screen shown in FIG. 12 appears on the monitor of the work station 6. Next, hospital-acquired retrieval data for identifying the emergency case, such as the name, the address, the ID number (e.g., the insurance number), etc., is entered (S12). The command processing unit 10 then makes access to the database management system 9 to search the medical information database 8 (S13). If, at this point, the database management system 9 is performing processing, then interrupt retrieval is performed. In the case of the retrieval mode, the system is forced to wait until the database management system 9 terminates the processing.

Next, on the basis of the result of retrieval, the command processing unit 10 makes a decision as to whether medical information about the emergency case is present or absent in the medical information database 8 of the hospital (S14). If YES, the command processing unit displays a list of bibliographical items of the case on the monitor of the work station 6 (S15). When a desired bibliographical item is selected from the list by the operator (S16), it is again accessed by the database management system 9, so that medical information including that bibliographical item is read out of the medical information database 8 (S17) and displayed on the monitor of the work station 6 (S18). Thus the command processing unit 10 terminates the emergency mode.

If NO in step S14, on the other hand, the command processing unit 10 changes the retrieval data and the emergency command into a transfer format and then transfers them to the medical information centralized management system 3 (S19).

The emergency command and the retrieval data are entered into the medical information centralized management system 3 (S20). The command processing unit 17 decodes the emergency command and starts the emergency mode. First, the command processing unit 17 makes a decision as to whether or not the emergency case resides in the areas within the jurisdiction of the medical information centralized management system 3 (S21). This decision is made by checking the case address with the table of cities, towns, and villages stored in the table memory 19. If NO in step S21, the command processing unit 17 displays on the monitor of the work station 6 a message describing that the case resides in another area outside of the jurisdiction of this system and transfers the retrieval data to the medical information centralized management system covering the area where the case resides after referring to the system ID table (S22), thus terminating the emergency mode. In the case where the area where the emergency case resides has no medical information centralized management system, or in the case where, even if there is a medical information centralized management system, it is not connected to the communication network 2, the emergency mode is terminated immediately.

Figure 10:
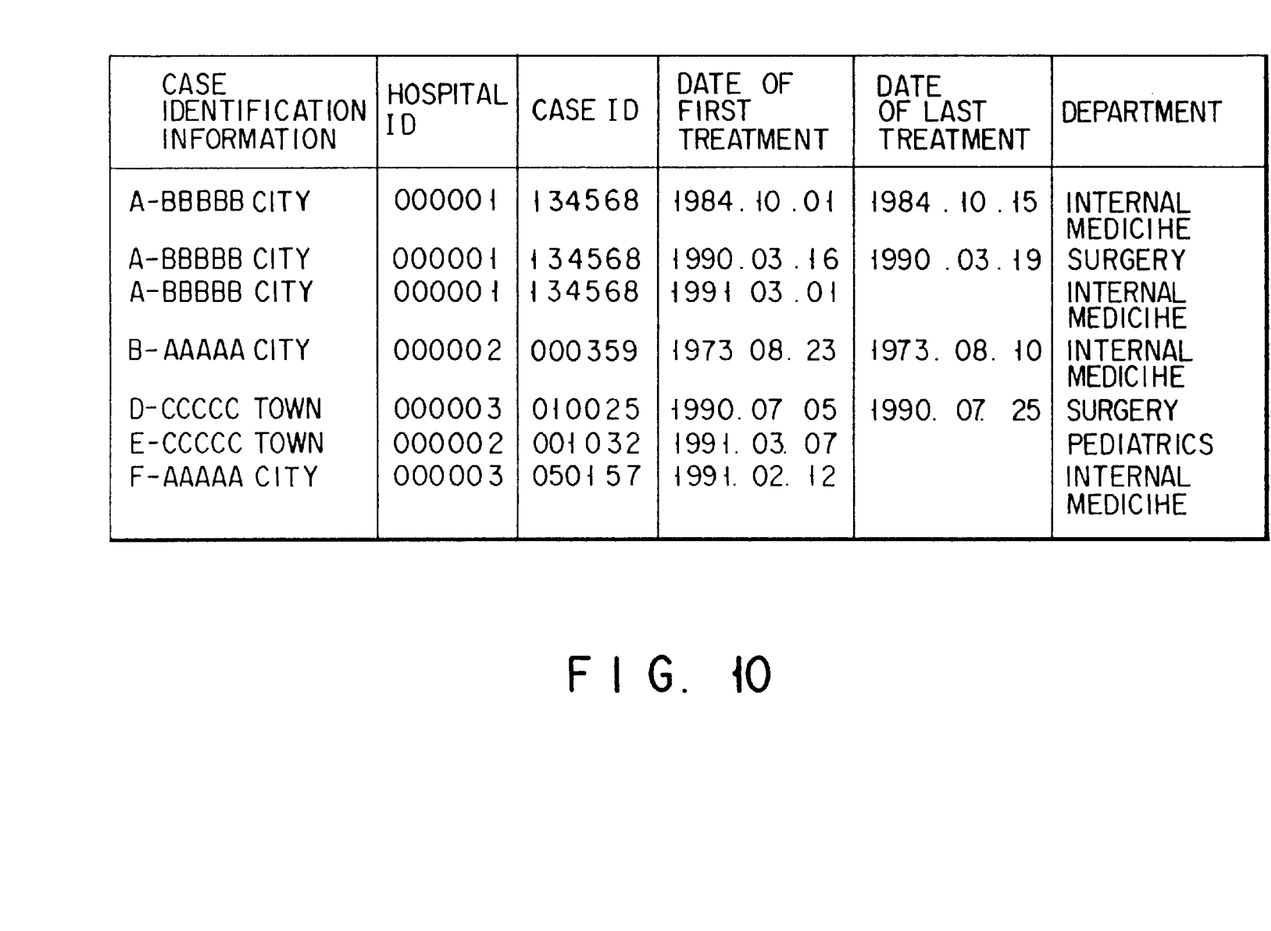
FIG. 10 shows a simplified hospital-attendance history file.

If YES in step S21, on the other hand, the command processing unit 17 makes access to the database management system 16 to retrieve the simplified history file shown in FIG. 10 from the simplified history file database 15 (S23). If, at this point, the database management system 16 is busy, interrupt retrieval is performed. In the case of retrieval mode, however, the system is forced to wait until the database management system becomes free.

Figure 13:
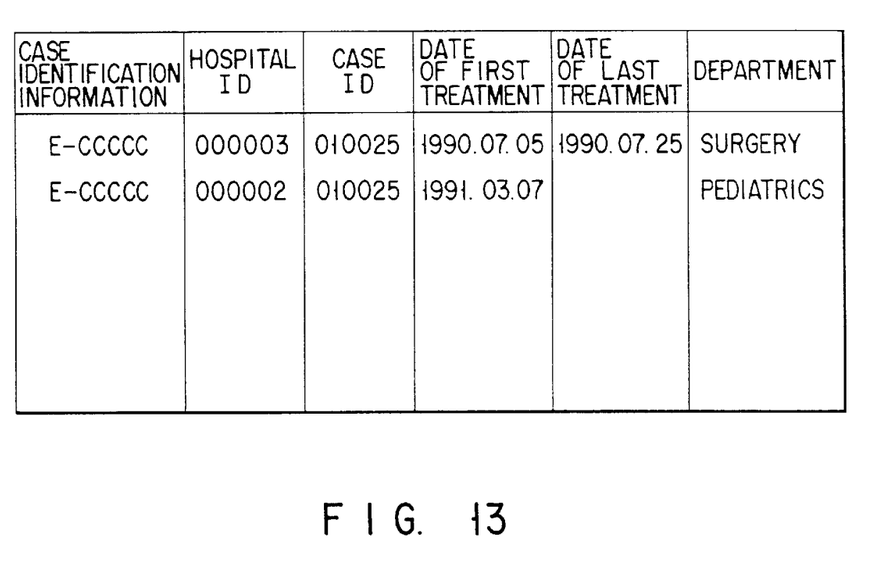
FIG. 13 shows a simplified hospital-attendance history list.

When all simplified history data corresponding to the retrieval data have been read out from the simplified history file database 15, the command processing unit 17 creates such a list of simplified history data as shown in FIG. 13 (S21) and returns it to the medical information storage system 1 which made the request for retrieval.

The medical information storage system 1 accepts the list (S26). This list is displayed on the monitor of the work station 6 by the command processing unit 10 (S27). Desired history data is selected by the operator (S28). The command processing unit 17 reads the hospital ID of a hospital that stores desired medical information from the selected history data and transfers the history data to the medical information storage system 1 specified by the hospital ID (S30).

When the destination medical information storage system 1 accepts the history data (S31), its command processing unit 10 retrieves a medical information file from the medical information database 8 by use of the history data (S32) and returns it to the requesting medical information storage system 1 (S33). The requesting medical information storage system 1 accepts the medical information (S34), which is then displayed on the monitor of the work station 6 by the command processing unit 10 (S35). Thus the emergency mode terminates.

As can be seen from the above, according to the present embodiment, medical information stored in all of hospitals located within unit areas is centrally managed by a medical information centrally management system on the basis of simplified history data composed of fundamental items which any hospital handles. Therefore, any hospital can acquire medical information stored by other hospitals with easy operations.

Although the embodiment was described as installing a medical information centralized management system in a central hospital located within a unit area, it may, of course, be installed in a hospital other than the central hospital. Moreover, if the work station 6 incorporates a security facility to start a mode only when a mode setting command and a password are received, security protection can be achieved easily. In this case, identification methods include fingerprint identification, voiceprint identification, retina identification, and gene identification besides password identification. Furthermore, although, in the present embodiment, a relatively wide area is made a range of management, the range of management may be brought within a hospital. In this case, data generated in various sections, such as a reception office, the internal department, the surgical department can be centrally managed by means of simplified history files.

A second embodiment of the present invention will be described next.

The recent spread of personal computers to homes has been remarkable. Many of the personal computers are connected to telephone lines. The second embodiment is intended to permit an efficient utilization of computer resources.

Figure 14:
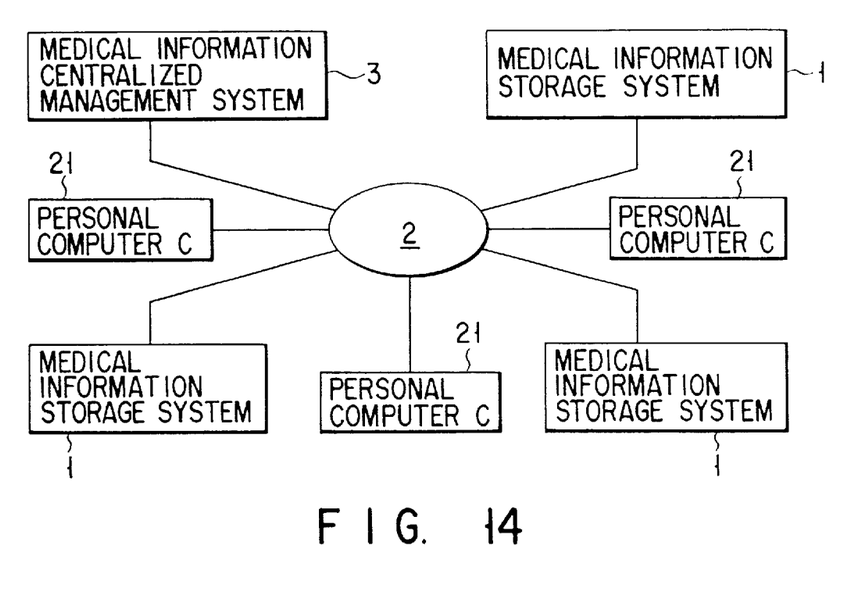
FIG. 14 is a block diagram of the entire system of a medical support system according to a second embodiment of the present invention.

FIG. 14 shows the entire configuration of the second embodiment. FIG. 14 corresponds to FIG. 1. Thus like reference numerals are used to denote corresponding parts and the description of them is omitted.

The medical support system of the second embodiment connects personal computers 21 for home use to the communication network 2. Simplified history data on a patient in a home is transferred from the medical information storage system 1 to the personal computer 21 in that home and stored in it. For this reason, the medical information centralized management system 3 stores a list of addresses of the personal computers in the table memory 19, the list being updated each time a fresh case comes to a hospital.

In the entry mode, simplified history data created by the medical information administration system 3 is entered into the simplified history file database 15. The history data is also transferred to the personal computer 21 in the home of the patient and entered into it.

Therefore, in case of emergency or at the time of retrieval, simplified history data can be transferred from a personal computer in the home of a patient to the medical information storage system 1 in a hospital receiving the patient. This saves time and labor taken to enter retrieval data into the medical information storage system 1, transfer the data to the medical information centralized management system 3, retrieve a simplified history file, and return the file to the medical information storage system 1. Thus it becomes possible to acquire desired medical information more quickly than in the first embodiment. With the second embodiment, there is no need for the medical information centralized management system 3 to manage simplified history files, permitting the scale of the medical information management system to be reduced.

A third embodiment of the present invention will be described hereinafter.

The third embodiment, like the second embodiment, is intended to reduce the time taken to acquire desired medical information.

With the first embodiment, in case of emergency or at the time of retrieval, the operator at a receiving hospital enters retrieval data into the medical information storage system 1 via the work station 6 after receipt of the name and address of an emergency case from an ambulance. The third embodiment saves time and labor taken to enter retrieval data after receipt of the case name and address.

Figure 15:
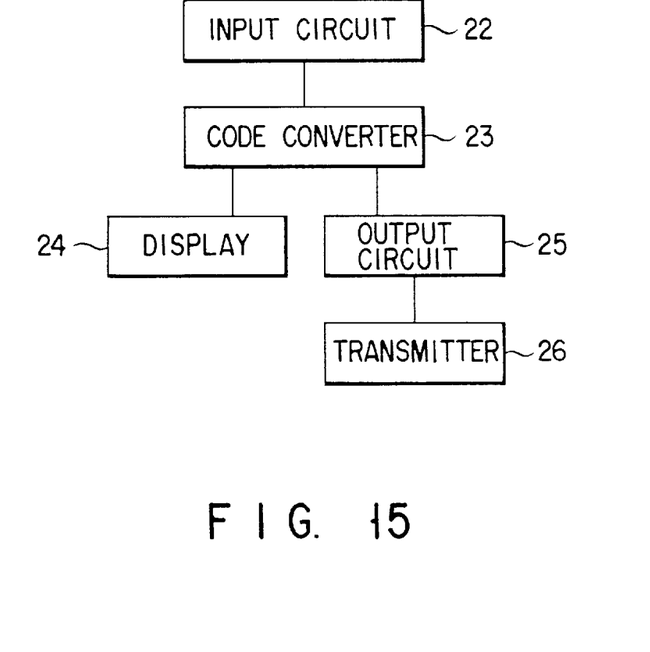
FIG. 15 is a block diagram of a transmitter that is carried aboard an ambulance used in a system according to a third embodiment of the present invention.

In the third embodiment, such a transmission unit as shown in FIG. 15 is carried aboard an ambulance. This unit is equipped with an entry device 33, such as a keyboard, for entry of retrieval data such as the case name and address, and a code converter 23 for encoding the retrieval data. The encoded data is displayed by a display device 24 for verification and sent to a wireless transmitter 26 via an output circuit 25. The transmitter 26 transmits the retrieval data to the medical information management system 3.

Figure 16:
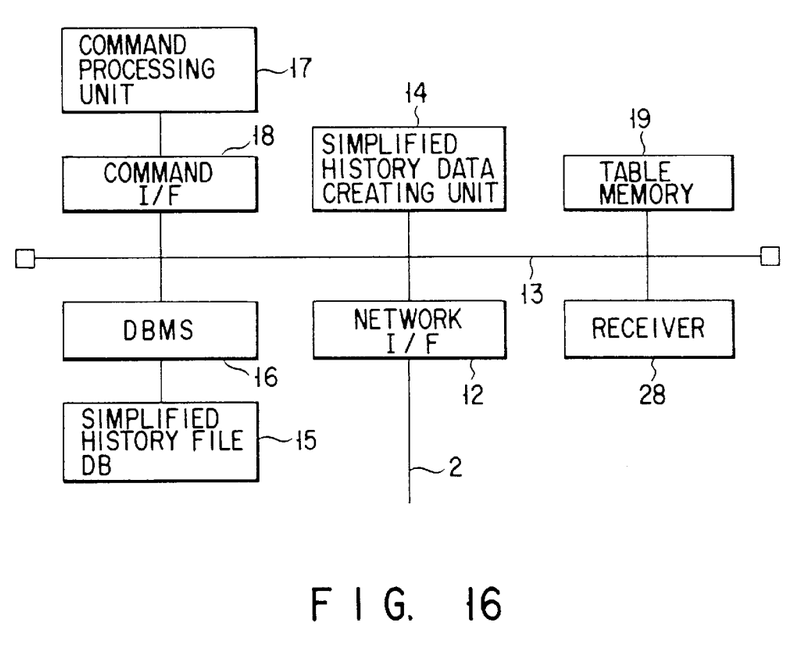
FIG. 16 is a block diagram of a medical information centralized management system in the third embodiment.

In order to receive the retrieval data transmitted by the transmitting unit, the medical information management system 3 is equipped with a receiver 28 as shown in FIG. 16. The command processing unit 17 in the medical information management system 3 refers on a simplified history file on the basis of the retrieval data, creates a simplified attendance history list of the case, and transfers the list to the medical information storage system 1 of a receiving hospital. The subsequent procedure is the same as the procedure following step S26 in FIG. 11B.

According to the third embodiment, therefore, there is no need for communication of the case name from an ambulance to a receiving hospital. This permits required medical information to be acquired more quickly than in the first embodiment. In addition, failure in communication from an ambulance to a receiving hospital can be eliminated.

A fourth embodiment of the present invention will be described hereinafter.

The fourth embodiment, like the second and third embodiments, is intended to reduce the time taken to acquire desired medical information.

Figure 17:
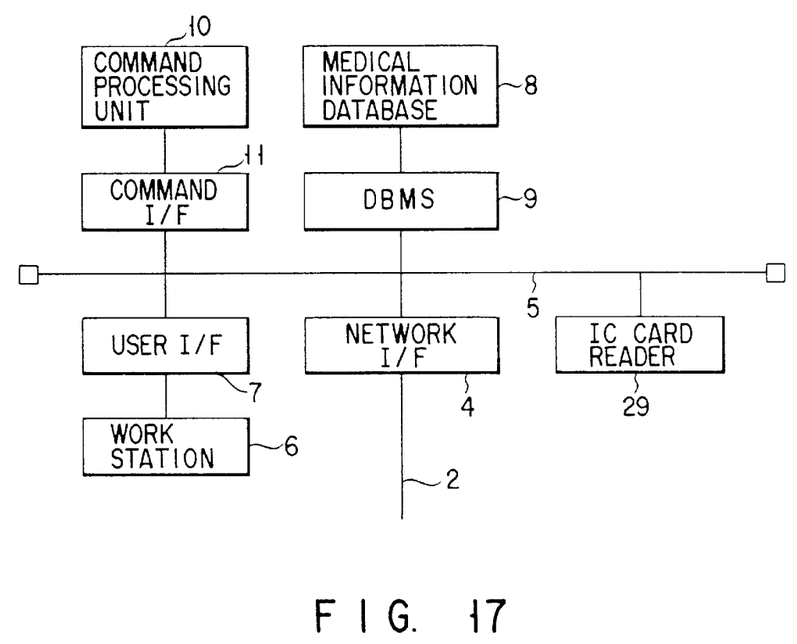
FIG. 17 is a block diagram of a medical information storage system according to a fourth embodiment of the present invention.
Figure 18:
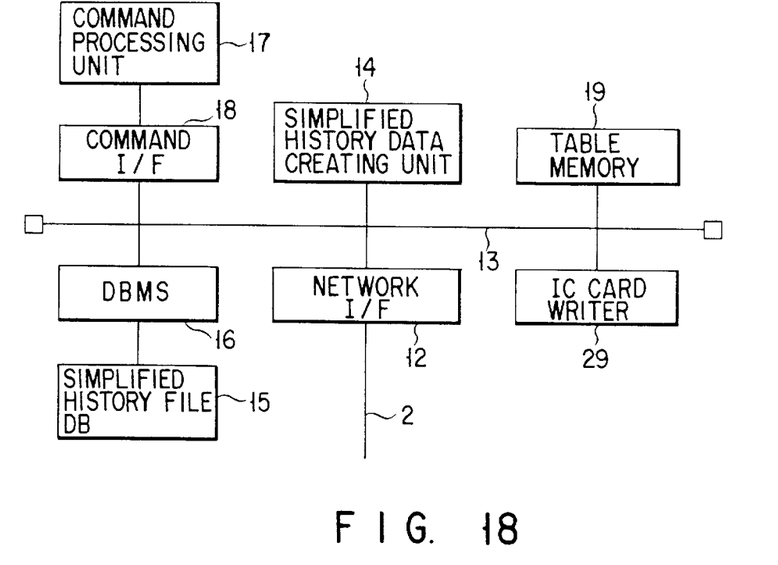
FIG. 18 is a block diagram of a medical information centralized management system in the fourth embodiment of the present invention.

FIG. 17 is a block diagram of a medical information storage system according to the fourth embodiment. FIG. 17 corresponds to FIG. 2. Thus, like reference numerals are used to denote corresponding blocks and the description of them is omitted. FIG. 18 is a block diagram of a medical information administration system according to the fourth embodiment. FIG. 18 corresponds to FIG. 3. Likewise, like reference numerals are used to denote corresponding blocks and the description of them is omitted.

As shown in FIG. 17, the medical information storage system 1 is equipped with an electronic smart card (IC card) reader 9. Also, the medical information management system 3 is equipped with a IC card writer 29 as shown in FIG. 18.

The IC card writer 29 writes simplified history data created by the simplified history data creating unit 14 in the medical information management unit 3 onto an IC card. An IC card is handed to a patient when he or she comes to a hospital within a unit area for the first time. The contents of the IC card are rewritten each time the patient attends at the hospital. In other words, a simplified attendance history list of the patient is stored on the IC card.

In retrieving medical information, the simplified attendance history list on the IC card is read by the IC card reader 29 in the medical information storage system 1 for display. The subsequent procedure is the same as that following step S26 in FIG. 11B.

According to the fourth embodiment, therefore, it becomes possible to reduce the time and labor taken to enter retrieval data into the medical information storage system 1, transfer the data to the medical information management system 3, retrieve the simplified attendance history file, and return the file to the requesting medical information storage system as in the first embodiment. This permits desired medical information to be acquired more quickly than in the first embodiment.

The IC card is a portable medium. Any other medium may be used as long as it can retain data. For example, usable mediums include magnetic cards, optical recording cards, ornaments (rings, necklaces, bracelets) embedded with ICs, etc.

Next, a fifth embodiment of the present invention will be described.

Depending on the condition, any patient cannot inform others of information for identifying himself or herself, for example, his or her name. Even in such a case, the fifth embodiment allows the acquisition of information that can be retrieval data such as name, insurance number, etc., thereby acquiring medical information.

Figure 19A:
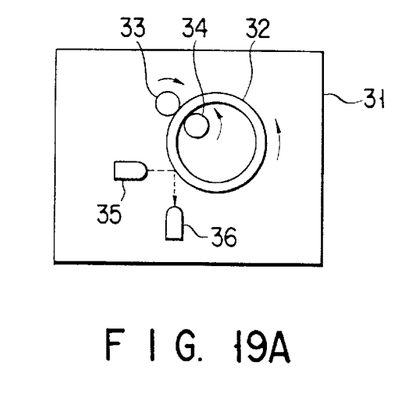
FIGS. 19A, 19B and 19C illustrate a reader used in a fifth embodiment of the present invention.

The fifth embodiment acquires information (here, name) about a patient that can be retrieval data and the hospital ID of the hospital that stores medical information about the patient from an ornament, e.g., a ring, which the patient usually wears. To this end, the ring is engraved with coded grooves representing the name and the hospital ID. The grooves may take the form of a bar code. A reader for reading the grooves on the ring is connected to the bus 2 in the medical information storage system 1.

Figure 19B:
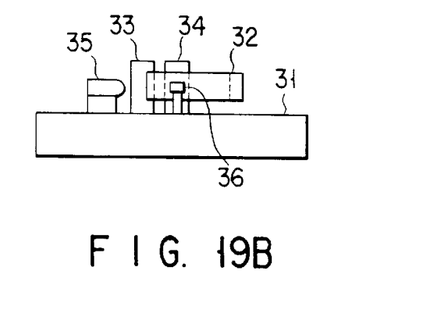
Figure 19C:
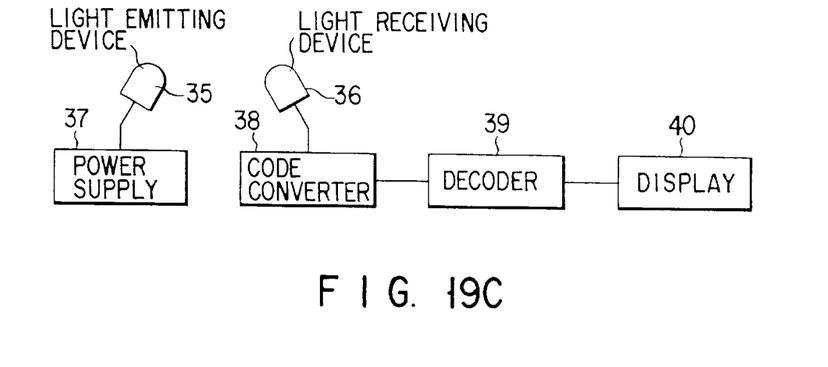

The reader is constructed as shown in FIGS. 19A, 19B and 19C. On a stand 31 is mounted a pair of rotating shafts 33 and 34 between which a ring 32 is caught. The shafts 33 and 34 are rotated in opposite directions by a driving source not shown, thereby rotating the ring 32 in the direction of an arrow shown. A light emitting device 35 and a light receiving device 36 are placed so that light emitted from the device 35 is reflected by the surface of the ring 32 and the reflected light from the ring surface is received by the device 36.

When powered by a power supply 37, the light emitting device 35 emits a beam of light onto the ring 35. Reflected light from the ring 32 is detected by the light receiving device 36, which produces a detect signal. The detect signal is converted by a code converter 38 to a code, which, in turn, is sent to a display unit 40 via a decoder 39. The display unit 40 visually displays the name and the hospital ID of the patient.

According to the fifth embodiment, therefore, even in the case of a patient who cannot inform others of even his or her name, the name and the hospital ID can be read from his or her ring. This permits medical information about the patient to be obtained in a short time.

According to the present invention, as described above, a medical support system can be provided which centrally manages a many of medical informations created by various hospitals or various sections, and permits medical information interchange among hospitals or among sections with easy operations.

Although the preferred embodiments of the present invention have been disclosed and described, it is apparent that other embodiments and modifications are possible. For example, the communication network in the above embodiments may be replaced by satellite communication.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A medical support system comprising:

plural local database systems located at different addresses, each of the plural local database systems comprising:

plural databases configured to store medical data of patients and retrieval data of the medical data in an individual manner, the retrieval data including addresses of the patients and IDs of the patients, and a management system corresponding to the plural databases of the local database system and configured to store a relationship between the addresses of the patients and system IDs of said plural local database systems, wherein one of the databases of the local database system is configured to determine, upon receiving a request for retrieving medical data of a patient, the request including the retrieval data of the patient, whether or not the medical data of the patient is stored in the one database based on the ID of the patient and is configured to transfer the request to the corresponding management system when the medical data is not stored in the one database, and wherein the corresponding management system is configured to determine, upon receiving the request from the one database, whether or not the medical data is stored in any of the plural databases in the local database system based on the ID of the patient and is configured to transfer the request to another management system of another local database system based on the address of the patient when the medical data is not stored in any of the plural databases in the local database system.

2. The medical support system according to claim 1, wherein the corresponding management system is configured to determine, when data registration is requested, whether or not the patient resides in a jurisdiction area corresponding to the management system based on the address of the patient, is configured to register the medical data with the retrieval data in the management system when the patient resides in the jurisdiction area, and is configured to transfer the medical data and the retrieval data to the other management system of the other local database system when the patient does not reside in the jurisdiction area corresponding to the management system.

3. The medical support system according to claim 1, wherein each of said plural databases is located in a different hospital and is connected to the corresponding management system via a network.

4. The medical support system according to claim 1, wherein the one database of the plural databases is configured to retrieve the medical data when the medical data is stored in the one database, and the corresponding management system receiving the request is configured to retrieve the medical data from the one database when the medical data is stored in the one database.

5. The medical support system according to claim 1, wherein each of the plural local database systems further comprises:

a terminal configured to input the retrieval data to the corresponding management system.

6. A management system for a medical support system, comprising:

a memory including a first field for storing locations within a jurisdiction area of the management system, a second field for storing locations of other management systems, and a third field for storing system IDs of the other management systems, each of the locations in the second field being associated with a corresponding one of the system IDs in the third field; and a processor configured to determine whether a patient resides within the jurisdiction area of the management system, upon receiving from a database within the jurisdiction area of the management system a request including residence information of the patient, by comparing the residence information of the patient with the locations stored in the first field, configured to identify another management system corresponding to one of the system IDs in the third field associated with one of the locations in the second field that matches the residence information of the patient when the patient resides outside the jurisdiction area of the management system, and configured to transfer the request to the other management system when the patient resides outside the jurisdiction area of the management system.

7. The management system according to claim 6, wherein the processor is further configured to register, when data registration is requested, medical data of the patient with retrieval data of the patient when the patient resides in the jurisdiction area of the management system, and is configured to transfer the medical data and the retrieval data to the other management system when the patient does not reside in the jurisdiction area of the management system.

8. The management system according to claim 6, wherein each of the databases corresponding to the management system is located in a different hospital and is connected to the management system via a network.

9. The management system according to claim 6, wherein the residence data and the locations stored in the first and second fields identify municipalities.

10. The management system according to claim 6, further comprising:

a terminal configured to input the retrieval data to the processor.

11. A method for managing a medical support system including plural local database systems located at different addresses, each of the plural local database systems including plural databases and a corresponding management system, said method comprising the steps of:

storing in the plural databases medical data of patients and retrieval data of the medical data in an individual manner, the retrieval data including addresses of the patients and IDs of the patients;

storing in the management system a relationship between the addresses of the patients and system IDs of said plural local database systems;

determining with one of the plural databases, upon receiving at the one database a request for retrieving medical data of a patient, the request including the retrieval data of the patient, whether or not the medical data of the patient is stored in the one database based on the ID of the patient;

transferring the request from the one database to the corresponding management system when the medical data is not stored in the one database;

determining with the corresponding management system, upon receiving the request from the one database, whether or not the medical data is stored in any of the plural databases of the local database system based on the ID of the patient; and transferring the request to another management system of another local database system based on the address of the patient when the medical data is not stored in any of the plural databases in the local database system.

12. The method according to claim 11, further comprising the steps of:

determining, when data registration is requested, whether or not the patient resides in a jurisdiction area corresponding to the management system based on the address of the patient;

registering the medical data with the retrieval data in the management system when the patient resides in the jurisdiction area; and transferring the medical data and the retrieval data to the other management system of the other local database system when the patient does not reside in the jurisdiction area of the management system.

13. The method according to claim 11, wherein each of said plural databases is located in a different hospital and is connected to the corresponding management system via a network.

14. The method according to claim 11, further comprising the step of:

retrieving with the one database of the plural databases the medical data when the medical data is stored in the one database; and retrieving with the corresponding management system the medical data from the one database when the medical data is stored in the one database.

15. The method according to claim 11, wherein each of the plural local database systems further comprises a terminal and the method further comprises the step of:

inputting the retrieval data to the corresponding management system with the corresponding terminal.

* * * * *